(12) United States Patent
Homsi

(10) Patent No.: US 10,315,070 B2
(45) Date of Patent: *Jun. 11, 2019

(54) CONSUMER USEABLE TESTING KIT

(71) Applicant: NIKE, Inc., Beaverton, OR (US)

(72) Inventor: Kristopher L. Homsi, Portland, OR (US)

(73) Assignee: NIKE, Inc., Beaverton, OR (US)

( * ) Notice: Subject to any disclaimer, the term of this patent is extended or adjusted under 35 U.S.C. 154(b) by 394 days.

This patent is subject to a terminal disclaimer.

(21) Appl. No.: 14/854,975

(22) Filed: Sep. 15, 2015

(65) Prior Publication Data

US 2016/0001132 A1   Jan. 7, 2016

Related U.S. Application Data

(63) Continuation of application No. 12/943,742, filed on Nov. 10, 2010, now Pat. No. 9,298,886.

(51) Int. Cl.
*A63B 41/00* (2006.01)
*A63B 24/00* (2006.01)
(Continued)

(52) U.S. Cl.
CPC ...... *A63B 24/0003* (2013.01); *A63B 24/0062* (2013.01); *A63B 41/00* (2013.01);
(Continued)

(58) Field of Classification Search
CPC .. G06F 19/3431; G06F 19/3481; G06F 19/00; A63B 41/00; A63B 24/0003; A63B 24/0062; A63B 2220/52; A63B 2220/20; A63B 2220/51; A63B 2102/22; A63B 2102/32; A63B 2102/18; A63B 21/4037; A63B 2243/0037; A63B 2243/0025; A63B 2225/50; A63B 2225/20; A63B 2225/15; A63B 2225/096; A63B 2220/836; A63B 2243/007; A63B 2220/806;
(Continued)

(56) References Cited

U.S. PATENT DOCUMENTS 5,761,096 A    6/1998  Zakutin
7,654,922 B2   2/2010  Vassilev et al.
(Continued)

FOREIGN PATENT DOCUMENTS

CN    101367011 A    2/2009
CN    101367013 A    2/2009
(Continued)

*Primary Examiner* — Joshua Lee
*Assistant Examiner* — Shila Jalalzadeh Abyaneh
(74) *Attorney, Agent, or Firm* — Banner & Witcoff, Ltd.

(57) ABSTRACT

Systems and techniques relating to evaluating performance characteristics are provided. One or more fitness devices, for example, a ball and/or a mat, may have sensors for measuring a user's actions during an activity protocol, such as a testing drill. Sensor configured to detect if the fitness device meets operational criteria are disclosed. In one embodiment, the fitness device may comprise a ball and the operational criteria may relate to the weight, dimensions, and/or internal pressure of the ball. In one embodiment, data from fitness device(s) may be used to calculate a score. In other embodiments, a score may be calculated; however, it may not be associated with credentials or certified if an operational criteria is not met.

7 Claims, 5 Drawing Sheets

(51) Int. Cl.
*G06F 19/00* (2018.01)
*G16H 50/30* (2018.01)
*A63B 71/06* (2006.01)
*A63B 102/24* (2015.01)
*A63B 102/32* (2015.01)
*A63B 21/00* (2006.01)
*A63B 102/22* (2015.01)
*A63B 102/18* (2015.01)

(52) U.S. Cl.
CPC .......... *G06F 19/00* (2013.01); *G06F 19/3481* (2013.01); *G16H 50/30* (2018.01); *A63B 21/4037* (2015.10); *A63B 2024/0012* (2013.01); *A63B 2024/0065* (2013.01); *A63B 2071/0694* (2013.01); *A63B 2102/18* (2015.10); *A63B 2102/22* (2015.10); *A63B 2102/24* (2015.10); *A63B 2102/32* (2015.10); *A63B 2220/12* (2013.01); *A63B 2220/13* (2013.01); *A63B 2220/20* (2013.01); *A63B 2220/30* (2013.01); *A63B 2220/40* (2013.01); *A63B 2220/51* (2013.01); *A63B 2220/52* (2013.01); *A63B 2220/56* (2013.01); *A63B 2220/72* (2013.01); *A63B 2220/806* (2013.01); *A63B 2220/833* (2013.01); *A63B 2220/836* (2013.01); *A63B 2225/096* (2013.01); *A63B 2225/15* (2013.01); *A63B 2225/20* (2013.01); *A63B 2225/50* (2013.01); *A63B 2243/007* (2013.01); *A63B 2243/0025* (2013.01); *A63B 2243/0037* (2013.01)

(58) Field of Classification Search
CPC ............ A63B 2220/72; A63B 2220/56; A63B 2220/40; A63B 2220/30; A63B 2220/13; A63B 2220/12; A63B 2071/0694; A63B 2040/0065; A63B 2024/0012; A63B 2220/833; A63B 2102/24; A63B 2024/0065; G16H 50/30
See application file for complete search history.

(56) References Cited

U.S. PATENT DOCUMENTS

| | | |
|---|---|---|
| 2006/0154758 A1 | 7/2006 | Laliberty et al. |
| 2007/0059675 A1 | 3/2007 | Kuenzler et al. |
| 2008/0088303 A1 | 4/2008 | Englert |
| 2008/0096726 A1 | 4/2008 | Riley et al. |
| 2008/0188353 A1 | 8/2008 | Vitolo et al. |
| 2008/0258921 A1 | 10/2008 | Woo et al. |
| 2010/0130315 A1 | 5/2010 | Steidle |
| 2010/0304866 A1 | 12/2010 | Lin et al. |
| 2011/0269517 A1 | 11/2011 | Englert et al. |

FOREIGN PATENT DOCUMENTS

| | | |
|---|---|---|
| EP | 1882499 A1 | 1/2008 |
| JP | 2009125509 A | 6/2009 |
| JP | 2010502368 A | 1/2010 |
| WO | 2008030484 A2 | 3/2008 |
| WO | 2010065886 A1 | 6/2010 |
| WO | 2010111705 A2 | 9/2010 |

CONSUMER USEABLE TESTING KIT

RELATED APPLICATIONS

This application is a continuation application that claims priority to Non-Provisional application, U.S. Ser. No. 12/943,742, filed Nov. 10, 2010, which is incorporated herein by reference in its entirety.

BACKGROUND OF THE INVENTION

Professional and amateur athletes alike strive to obtain a level of athletic ability. Unfortunately, however, their chosen exercise routines may not allow the athlete to excel to their full potential. Further, individuals without experienced coaches or trainers are even less likely to reach their full potential. Thus, merely following a standard exercise routine will not assist the individual to improve certain performance characteristics that may be important. For example, an individual who desires to play football for a professional sports team may have adequate speed to be considered a possible member of the team or league; however, his responsiveness to a sport or fitness-related response may be below acceptable ranges. Blindly following an improper exercise routine may not improve his responsiveness.

Further, coaches and recruiters need to quickly determine the performance characteristics of several individuals in a relatively short period of time. Although they may receive recordings or statistics of possible players, most likely do not provide an accurate evaluation into pertinent characteristics, such as speed, responsiveness, quickness, and power, among others. Further, statistics may be fabricated or inaccurate. Even when attempting to accurately measure performance characteristics, high levels of uncertainty may be present given the unknown condition of timers, equipment, and other variables. Further, each athlete's performance may have been measured with different timers, equipment, and/or environmental conditions.

Certain systems and methods may provide certified ratings of athletes; however, current systems and methods are expensive and time-intensive. For example, current systems and methods require training people to administer a plurality of testing protocols. Further, given the costs and time-intensive process of training, calibrating equipment, traveling to various locations, and conducting the analysis, the process is cost and time prohibitive for many athletes.

Further, amateur athletes may not pursue such testing or analysis. This is unfortunate, because improvements in athletic performance, even for non-competitive individuals, tend to encourage continued exercise. Unfortunately, without proper analysis and testing, an individual may not improve desired athletic qualities. Further, relying only on physical improvements obtained from exercise often results in failure as many physical improvements takes several weeks or months to appear, and thereby provide insufficient motivation to maintain a exercise program. For example, it may take an extended period of time for an individual to physically notice what qualities are improving and what qualities are not improving. Furthermore, without accurate systems and methods for measuring their performance, the individual may incorrectly evaluate one or more performance characteristics. Therefore, for these and other reasons, there is a need for improved systems and methods.

BRIEF SUMMARY

The following presents a general summary of aspects of the invention in order to provide a basic understanding of the invention and various features of it. This summary is not intended to limit the scope of the invention in any way, but it simply provides a general overview and context for the more detailed description that follows.

Aspects of this invention relate to systems and methods for evaluating athletic performance characteristics of a user. According to certain embodiments, one or more fitness devices may be detected. Any component or collection of components configured to measure a fitness parameter may be a fitness device according to embodiments disclosed herein. For example, a fitness device may include components required for or otherwise commonly associated with a specific physical activity, such as balls, pucks, discs or the like. For example, in one embodiment, a fitness device may comprise a ball, such as a medicine ball. Yet in other embodiments, a fitness device may include objects within the environment where the physical activity occurs, including the environment itself, such as a goal marker or a mat that a user may be positioned on. Further exemplary embodiments are discussed in more detail below when discussing specific embodiments. One or more fitness devices may be utilized together in a system. For example, a medicine ball may comprise a sensor configured to measure a first parameter and a second fitness device, such as a mat, may comprise at least one sensor configured to measure a second parameter.

Further aspects relate to sensors configured to detect if the fitness device meets operational criteria. In one embodiment, the fitness device may comprise a ball and the operational criteria may relate to the weight, dimensions, and/or internal pressure of the ball. In certain embodiments, the ball (or other fitness device) may not collect data relating to a fitness parameter if a portion of the operational criteria is not met. In other embodiments, the fitness device may collect data from one or more sensors; however, usage of the data may be restricted. In one embodiment, data from the relevant fitness device may not be used to calculate a score. In other embodiments, a score may be calculated; however, it may not be associated with credentials or certified if certain operational criterion is not met.

Further aspects relate to systems and method for conducting an activity protocol with a fitness device. The activity protocol may be selected from a plurality of activity protocols. In one embodiment, the selection may be based, at least in part, a detected fitness device or collection of fitness devices, a sensor of a detected fitness device, a parameter measured by a detected fitness device, and combinations thereof.

A plurality of performance characteristics may be calculated that relate to a user's performance of an activity protocol. For example, in one embodiment, the performance characteristics are selected from the group consisting of: power, agility, speed, reaction, and/or quickness. In certain embodiments, data collected from sensors on several fitness devices may be cross-referenced to validate data. For example, data relating to: timing between two user actions, timing of a specific user action, location of a user, location of a fitness device, velocity of a user, velocity of a fitness device, acceleration of a user, acceleration of a fitness device, detection of a sensor, and/or detection of a fitness device may be validated by comparing data collected or otherwise derived from the sensors of the fitness devices. In certain embodiments, a score may be calculated from verified data.

Further aspects relate to standardizing fitness devices and the user's performance during activity protocols. For example, in one embodiment, a fitness device may comprise a mat and an apparatus (which may or may not be a fitness device) may comprise footwear. In one embodiment, the mat may include one or more sensors configured to detect pressure from the footwear and determine if the footwear comprises unauthorized pressure points, such as spikes. In certain embodiments, such systems and methods may prevent cheating and/or ensuring that multiple users utilize similar fitness devices in a consistent manner during one or more activity protocols. In other embodiments, certain features (for example, protocols available for selection and/or calculation of a specific score) may be disabled or otherwise unavailable if certain devices are not detected. For example, a certified score may not be calculated, if a ball (such as, for example, a medicine ball) is not detected. In another embodiment, a certified score may not be collected if a specific sensor (for example, on a medicine ball) is not detected.

In accordance with various embodiments, fitness devices may have one or more replaceable sensors. In one embodiment, a medicine ball may comprise a replaceable t-axis accelerometer that may be replaced with a 3-axis accelerometer. In certain embodiments, detection of certain sensors, such as an accelerometer may be utilized in the selection of an activity protocol from the plurality of activity protocols. Further embodiments may detect that the replacement sensor is a different type of sensor than the original sensor. Further embodiments may adjust the property of a fitness device based upon a detected property of another fitness device.

Further aspects relate to a ball fitness device with a first sensor configured to measure a fitness parameter. The ball may have a second sensor configured to measure a first operational criterion of the ball. A wireless transceiver of the ball may transmit data collected from the first and second sensors. The ball may be configured to communicate with a system having a memory with computer-executable instructions. The instructions may determine whether the first operational criterion is not met. In certain embodiments, a feature of the system, including a feature of the ball, may be disabled or otherwise not fully functional. For example, in one embodiment, the collection of data and/or the utilization of data to calculate a score may be disabled. In certain embodiments, data from the sensors of the ball may be used to calculate a performance characteristic, such as for example, power, agility, speed, reaction, quickness, and combinations thereof. Certain data may relate to for example: distance traveled, velocity in flight, and/or power upon impact.

The ball may be configured to communicate with one or more other fitness devices. In one embodiment, the calculation of at least one performance characteristics comprises the utilization of data from two or more fitness devices. In one embodiment, a performance characteristic is calculated from data from a ball's sensor and a mat's sensor.

These and other features of the invention will become apparent from the following detailed description.

BRIEF DESCRIPTION OF THE DRAWINGS

A more complete understanding of various aspects disclosed herein and certain advantages thereof may be acquired by referring to the following detailed description in consideration with the accompanying drawings, in which.

The reader is advised that the attached drawings are not necessarily drawn to scale.

DETAILED DESCRIPTION

In the following description of various example structures and methods in accordance with the invention, reference is made to the accompanying drawings, which form a part hereof, and in which are shown by way of illustration various fitness devices and systems using fitness devices in accordance with various embodiments of the invention. Additionally, it is to be understood that other specific arrangements of parts and structures may be utilized and structural and functional modifications may be made without departing from the scope of the invention.

Aspects relate to fitness devices having one or more sensors. As used herein, the term "fitness device" includes any physical object that may be used or implicated, during physical activity, for example a sport or training drill. In certain embodiments, one or more fitness devices may be held, attached or worn by a user. Exemplary devices may include, clothing such as shoes, shirts, shorts, gloves, hats, or electronic devices, such as watches, telephones, media players, among others. In one embodiment, a fitness device may be attachable to a user's shoe. In another embodiment, a device may be attachable to a user's arm, such as similarly performed by a watch, ring, or graspable by a hand, such as any handheld electronic device, including mobile terminal devices and/or personal media players.

Further exemplary fitness devices may include components required for or otherwise commonly associated with the physical activity. Exemplary fitness devices may include, but are not limited to: golf balls, basketballs, baseballs, soccer balls, footballs, balls, hockey pucks, weights, bats, clubs, sticks, paddles, mats, and combinations thereof. In further embodiments, exemplary fitness devices may include objects within the environment where the physical activity occurs, including the environment itself, such as a goal net, hoop, backboard, portions of a field, such as a midline, outer boundary, end zone, field goal marker, base, and combinations thereof.

Figure 1:
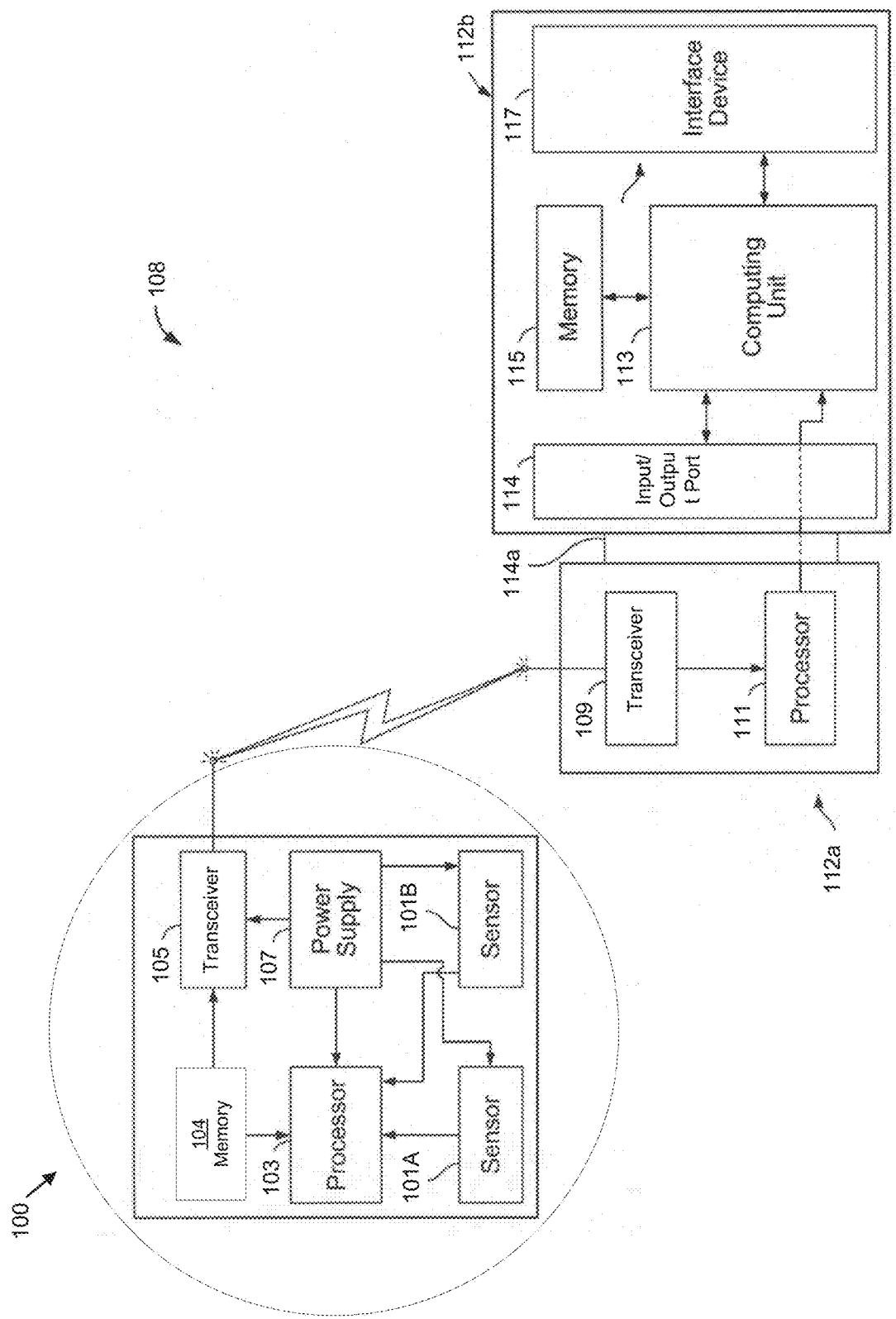
FIG. 1 illustrates an exemplary computing environment that may be used to implement various examples of the invention.

FIG. 1 shows exemplary fitness device 100 in accordance with one embodiment disclosed herein. Exemplary fitness device 100 may be a ball having a spherical shape. Fitness device 100 may comprise one or more sensors, such as sensors 101A and 101B (collectively referred to as sensors 101). Sensors 101 may include any apparatus(es) configured to detect a stimulus and provide a resulting signal. In certain embodiments, sensors 101 may be utilized to measure one or more parameters, such as, for example, velocity, acceleration, pressure, location, energy transfer, temperature, orientation, light, sound, magnetism, or a particular motion along two or more axes.

In one embodiment, sensors 101 may comprise an accelerometer module. In one embodiment, the accelerometer module may be implemented with a two-axis accelerometer for measuring acceleration along two orthogonal axes. In another embodiment, the accelerometer module may be implemented with a three-axis accelerometer for measuring acceleration along three orthogonal axes. Further exemplary sensors may include strain gauges, conductive ink, piezo-electric devices and/or pressure transducers. In certain embodiments, relative pressure applied to two or more sensors 101 can be used to indicate weight distribution. Yet, in other embodiments, pressure detected or measured by one or more sensors 101 may be used to detect grip, such as gripping a ball or bat.

As shown in FIG. 1, one or more sensors 101 may be embedded within the fitness device 100. In this regard, sensors may be positioned within an outer layer of fitness device. This may be advantageous to protect sensors 101 and/or to prevent tampering with the sensors 101. In other embodiments, one or more sensors 101 may not be fully embedded within fitness device 100. This may be advantageous, for example, to obtain accurate measurements from sensors 101. Regardless of whether one or more sensors 101 are fully or partially encased within fitness device 100, one or more sensors 101 may be removable and/or interchangeable. This implementation may be useful for one or more reasons, for example, to readily permit the replacement of faulty or aged sensors. It also may permit fitness device 100 to be utilized in various activities. For example, fitness device 100 may comprise a ball and sensor 101A may include a removable accelerometer module that is configured to detect acceleration within a first range commonly associated with professional athletes performing a specific activity. The accelerometer module may be replaced with a different sensor (i.e., pressure sensor) that is configured to detect a parameter commonly associated with professional athletes performing a different activity. Moreover, while sensor 101A is shown physically separate from 101B, those skilled in the art with the benefit of this disclosure will readily appreciate that two or more sensors, such as sensors 101 may be provided on a single component.

Using removable sensors may permit a sensor, such as sensor 101A to be used with several different fitness devices, such as soccer balls, medicine balls, footballs, and/or allowing a user to upgrade or replace a faulty device, such as medicine balls without having to obtain a new sensor. In certain embodiments, placement of one or more sensors 101 may be configured so that the weights of the included sensors 101 do not change the balance or center of gravity of the fitness device 100.

In certain embodiments, sensor 101A may be of the same type as sensor 101B. For example, in one embodiment, sensors 101 may each be accelerometers. In other embodiments, sensor 101A may be similar, but not the same as, sensor 101B. For example, sensor 101A may comprise a first accelerometer configured to detect acceleration within a first range, and sensor 101B may comprise a second accelerometer configured to detect acceleration within a second range. In certain embodiments, the first range may overlap or otherwise be inclusive of values within the second range detectable by the second accelerometer. In still yet other embodiments, sensors 101 may measure different parameters. For example, in one embodiment, sensor 101A comprises an accelerometer and sensor 101 may comprise a pressure sensor.

Sensors 101 may be active or passive. For example, in certain embodiments, one or more sensors may actively transmit or provide an output, such as a wireless signal that may be used in the detection of a parameter. For example, sensors 101 may comprise electromagnetic devices, such as wireless sensors, including for example radio frequency, electromagnetic and/or optical sensors. In one embodiment, one or more sensors may be implemented with microstrip antennas. Yet, in other embodiments, sensors 101 may comprise a passive sensor configured to detect and/or measure a stimulus. Regardless of whether sensors 101 are active or passive, sensors 101 may detect stimuli or a result of stimuli transmitted by another sensor of either fitness device 100 or another device, such as a second fitness device, or a non-fitness device. Power to sensors 101 may be provided by power supply 107 (which is discussed below).

Fitness device 100 may comprise processor 103 and/or memory 104. Memory 104 may comprise read-only memory (ROM) and/or random access memory (RAM). As will be appreciated by those of ordinary skill in the art, memory 104 may store computer-implemented instructions for execution by a processor, such as processor 103. In certain embodiments, processor 103 may be configured to process output transmitted from sensors 101. Processor 103 may be a programmable microprocessor, yet in other embodiments, processor 103 may be a purpose-specific circuit device, such as an ASIC. In certain embodiments, memory 104 may comprise computer-executed instructions that when executed by a processor, such as processor 103, may be configured to cause the performance of one or more operations. Exemplary computer-executable instruction may include performing operations on the output from sensors 101, such as curve smoothing, noise filtering, outlier removal, amplification, summation, integration, or the like. While memory 104 and processor 105 are shown as being located within device 100, those skilled in the art will readily appreciate that either memory 104 and/or processor 105 may be external to fitness device 100.

In certain embodiments, processor 103 may be in operative communication with, and as such may provide processed or raw signals to, transceiver 105 for transmission to an electronic device, such as device 108. In certain embodiments, power supply 107 may be configured to provide power to transceiver 105, memory 104, processor 103 and/or sensors 101. The power supply 107 may be configured to accept either alternating current (AC) and/or direct current (DC). In certain embodiments, power supply 107 may comprise a converter for converting energy between AC and DC power.

Electronic device 108 may comprise transceiver 109 configured to communicate with transceiver 105 of the fitness device 100. In other embodiments, transceiver 109 may be configured to communicate with other fitness devices in addition to or in lieu of fitness device 100. In certain embodiments, receiver 109 may be in operative communication with a processor, such as processor 111. For example, transceiver may transmit signals, such as raw or processed sensor data, to processor 111. Similar to processor 103, processor 111 may perform any desired operation on the processed signals, such as curve smoothing, noise filtering, outlier removal, amplification, summation, integration, or the like.

Electronic device 108 may comprise two detachable components, 112a, 112b. For example, component 112a may be a relatively smaller component than component 112b. For example, in one embodiment, component 112b is a mobile terminal device and/or a personal media player and component 112a provides further functionality to the component 112b. Component 112a may connect to component 112b such that processor 111 may communicate with computing unit 113 of the electronic device 108. Processor 111 may communicate directly with computing unit 113 directly, and in certain embodiments, be a part of computing unit 113. Component 112a may also communicate with computing unit 113 and other portions of component 112b through input/output (I/O) interface 114, using one or more channels, such as channel 114a. In certain embodiments, for example, where 112a is not detachable, I/O interface may be excluded. Further, processor 111 of component 112a and/or computing unit 113 of component 112b may be redundant or otherwise not required in certain embodiments.

Computing unit 113 may comprise a processor configured to read and/or write data to memory 115. Exemplary data may include raw or processed signals from sensors 101. Computing unit 113 may further operate on processed signals provided by one or more fitness devices, such as fitness device 100, for example, to generate a set of athletic data corresponding to athletic activity performed by a user. In certain embodiments, computing unit 113 may execute computer-executable instructions located on a memory, such as memory 115. Exemplary computer-executable instructions may include one or more processes discussed below in relation to FIGS. 2, 4 and/or 5.

Electronic device 108 may further comprise I/O interface device 117. I/O interface device 117 may comprise one or more ports or interfaces (or devices connected through such ports or interfaces) configured to receive an input or transmit an output from device 108. In certain embodiments, I/O interface device 117 may comprise a peripheral device permanently or semi-permanently connected to the computing unit 203. For example, with many computers, the computing unit 113, memory 115, are semi-permanently encased in a housing. In certain embodiments, such as mobile terminal devices or personal media players, a display may also be within the housing. In yet other embodiments, one or more other peripheral devices, such as a removable memory and/or a display may be removably connected to the computer. Interfaces or ports of the I/O interface device 117 may include, for example, one or more communication ports through which a peripheral device can be in operative communication with computing unit 113 (either directly or indirectly through, for example, a bus). Exemplary communication ports may include a parallel bus port or a serial bus port, such as a serial bus port using the Universal Serial Bus (USB) standard or the IEEE 1394 High Speed Serial Bus standard (e.g., a Firewire port). Alternately or additionally, I/O interface device 117 device may include a communication port configured to communicate with a network. In certain embodiments, I/O interface device 117 may comprise a wireless data "port," such as a Bluetooth interface, a Wi-Fi interface, an infrared data port, or the like.

It should be appreciated that electronic device 108 is merely exemplary and that various embodiments within the scope of this disclosure may include more or fewer components than electronic device 108 illustrated in FIG. 1. In certain embodiments, electronic device 108 may include specific functionality, such as a server computer at a fitness center. Such specialized devices may thus omit unnecessary peripherals, such keyboards and/or mice, however, comprise further devices, such as specialized or multiple communication connections. Other exemplary embodiments of electronic device 108 may alternately or additionally employ computing devices that are intended to be capable of a wide variety of functions, such as a desktop or laptop computer. These computing devices may have any combination of peripheral devices or additional components as desired.

Further aspects disclosed herein relate to standardizing or normalizing fitness devices, such as fitness device 100. In certain embodiments, one or more sensors may be configured to detect performance parameters of a user utilizing one or more fitness devices to standardize one of the fitness devices being used. In certain embodiments, standardized or normalized fitness equipment may be configurable to measure specific actions of a user of the fitness equipment. In certain embodiments, one or more sensors may be configured to detect improper usage. In one embodiment, two or more fitness devices may be utilized in a networked environment.

Figure 2:
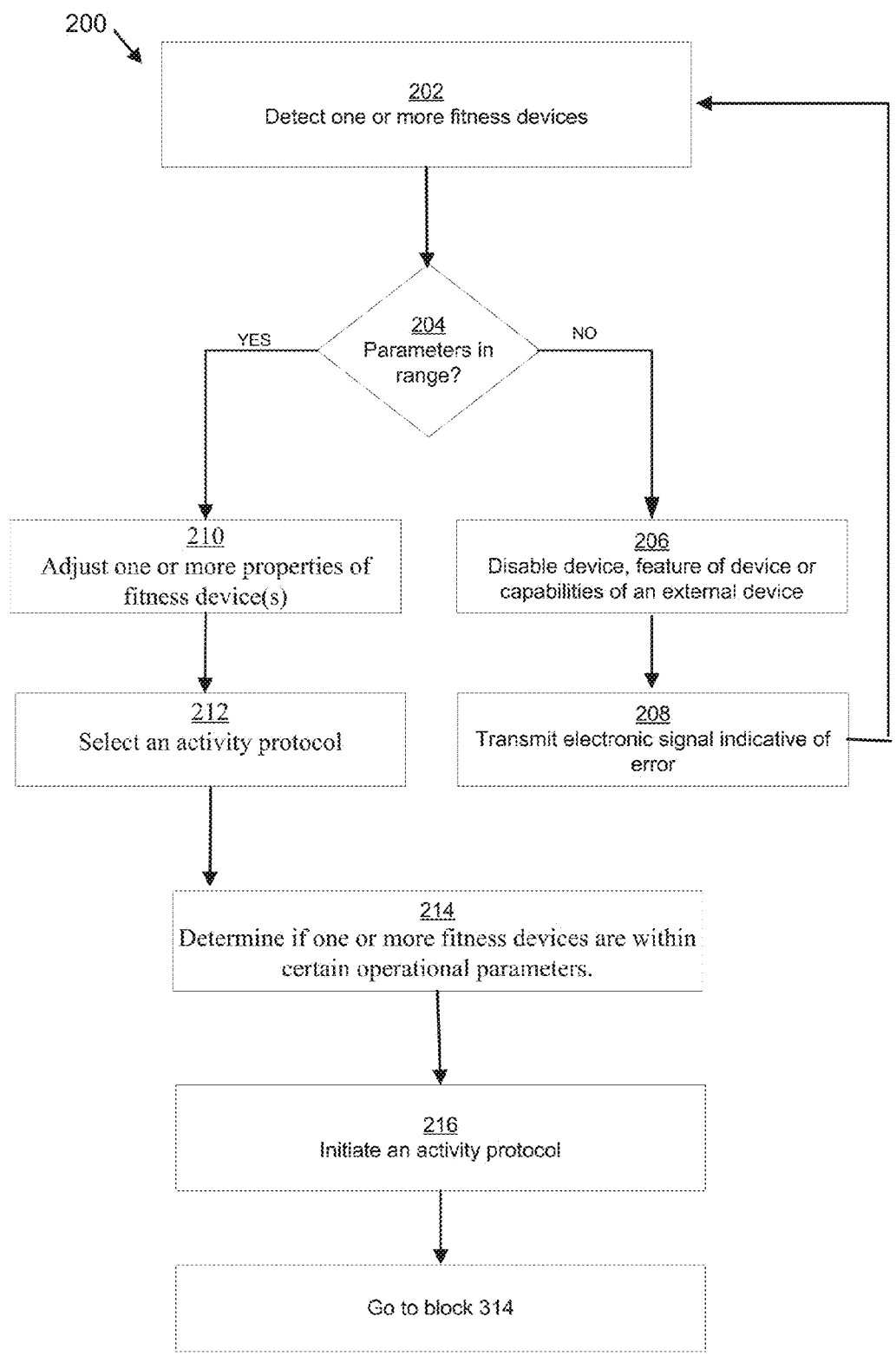
FIG. 2 is a flowchart of an exemplary method that may be implemented according to various embodiments of the invention.
Figure 3:
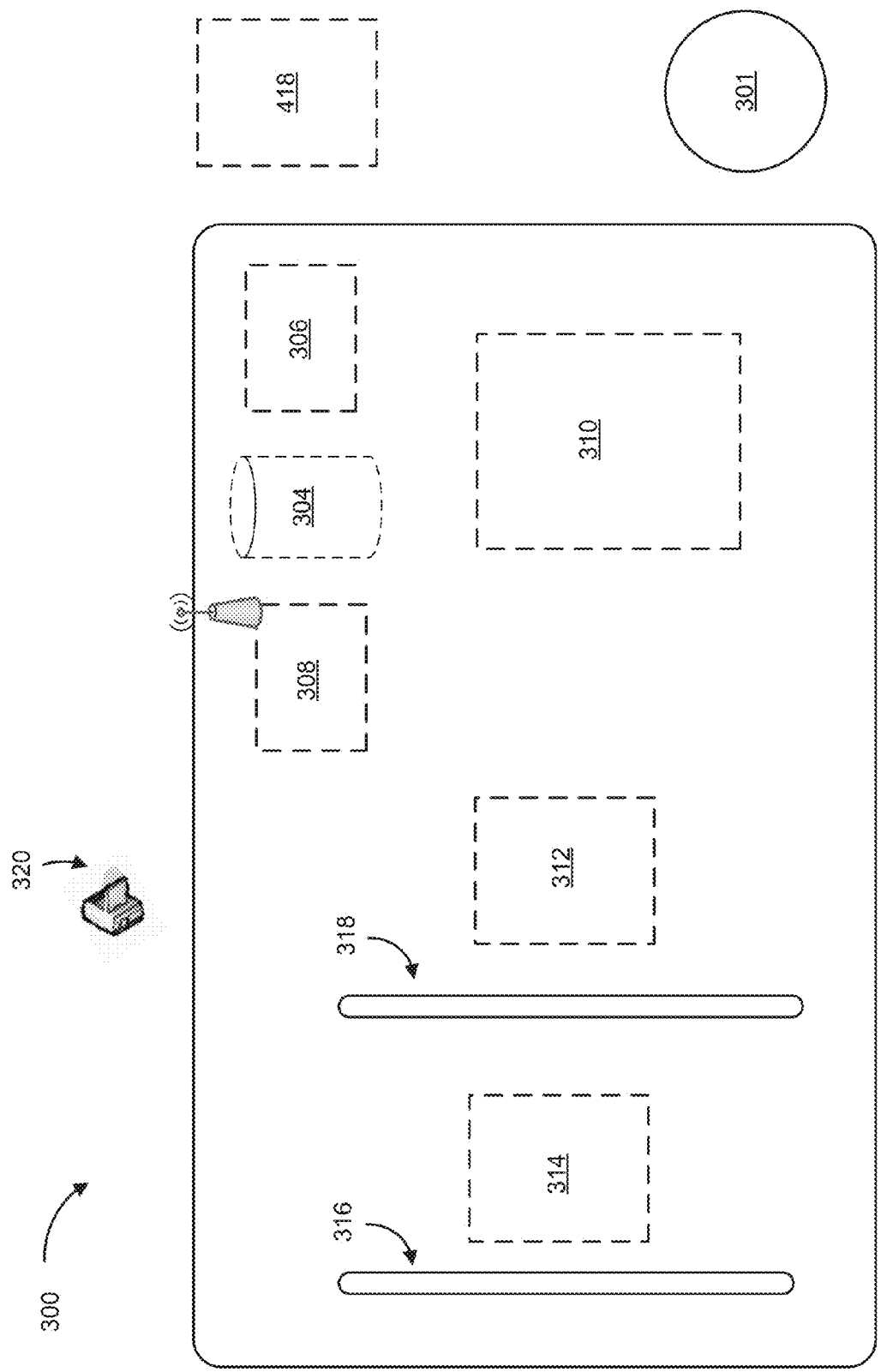
FIG. 3 is an exemplary system having one or more fitness devices according to various embodiments of the invention.

FIG. 2 is a flowchart 200 showing an exemplary method that may be used in accordance with various embodiments of the invention. Flowchart 200 may be used in conjunction with the fitness device 100 shown in FIG. 1 or any other device having a sensor configured to detect or measure a parameter. In certain embodiments, flowchart 200 may the performed in connection with a system having a plurality of sensors. Therefore, exemplary uses of certain embodiments of flowchart 200 of FIG. 2 will be explained in conjunction with system 300 of FIG. 3. For example, block 202 may be implemented to detect fitness devices. Looking to system 300 of FIG. 3, two fitness devices, fitness ball 301 and mat 302 are shown. Ball 301 may be a power or exercise ball in certain embodiments. In certain embodiments, ball 301 may be substantially similar to fitness equipment 100 of FIG. 1, and as such, ball 301 may comprise one or more components shown in FIG. 1. Therefore, while not explicitly shown in FIG. 3, reference to individual components 101-108 of ball 301 is made below when describing certain embodiments disclosed herein. System 300 may further comprise additional fitness equipment, such as mat 302. Like ball 301, mat 302 may comprise one or more components shown in the exemplary fitness device 100 of FIG. 1.

Implementation of block 202 may permit the detection of ball 301, mat 302, and/or other fitness devices of system 300. As discussed below, ball 301, mat 302 and/or other fitness devices may be marketed together as a kit. In certain embodiments, mat 302 may comprise memory 304. Memory 304 may comprise computer-readable instructions that include a value permitting the identification of mat 302. The computer-executable instructions may be executed by a processor, such as processor 306 and transmitted, such as by transceiver 208 to a computing device. Memory 304, processor 306, and transceiver 308 are shown as dotted lines in FIG. 3 to designate that they may be embedded within mat 302. In certain embodiments, mat 302 may comprise a protective chamber or housing that protects electronic components, including components 304-308 from damage. Similarly, memory 104 of ball 301 may store a value that permits identification of ball 301.

Values representing fitness devices, such as for example, ball 301 and/or mat 302 may comprise a unique value. The unique value may comprise a serial number assigned to that specific device or a kit in which the device is a part of Yet in other embodiments, a value may not be unique but rather may generically refer to a genus of devices. For example, the value may be a function of a characteristic of the fitness device. In one embodiment, balls weighing 6.6 pounds may be assigned a certain value and balls weighing 3.3 pounds may be assigned a different value. In other embodiments, fitness devices, such as ball 301, designed for particular purposes may be assigned a specific value. In another embodiment, values may allow the manufacturer or supplier of the device to be identified. In certain embodiments, values may comprise both unique identifier and a generic identifier. For example, the value may comprise a unique serial number (or portion thereof) and also a generic identifier that is assigned to devices having a specified characteristic.

Values may be received at a computing device, such as electronic device 108. In one embodiment, memory 115 may comprise computer-executable instructions that when executed by a processor, such as computing unit 113, allow detection of one or more fitness devices in system 300. In this regard, memory 115 may comprise software having one or more features that may depend on detected fitness devices. For example, upon detecting of certain fitness devices, such as ball 301 or mat 302, certain features may be available, whereas if ball 301 and/or mat 302 are not detected, at least a portion of the features may not be enabled or fully functional. As explained later in this disclosure, including for example when describing block 514 of FIG. 5, aspects of this disclosure relate to calculating a score based upon sensor data. Such features, however, may be disabled or otherwise not available if certain fitness devices are not detected.

Further aspects relate to systems and methods to normalize or standardize fitness equipment. Implementing such systems and methods may be advantageous for several reasons, including but not limited to the fact that using improperly configured equipment may be dangerous or hazardous to not only the user but to any spectators. Further, if the fitness equipment is being used to measure performance characteristics of a user to provide a score, it would be beneficial to ensure that the equipment provided to each user being scored was normalized or standardized to ensure meaningful results.

In certain embodiments, block 204 may be conducted to determine if one or more fitness devices are within certain operational criteria or parameters. In one embodiment, sensors 101 of ball 301 may comprise a pressure sensor to detect the internal pressure of ball 301. In this regard, if the pressure is above a threshold, a user may not adequately grip the ball to perform certain tasks. Likewise, if the internal pressure of ball 301 is below a threshold, the user may have an unfair advantage by having an increased grip on it. In another embodiment, mat 302 or another fitness device may detect or measure a property of another fitness device. For example, in one embodiment, mat 302 may comprise a sensor, (i.e., sensor 310) configurable to measure a parameter of ball 301. In one embodiment, sensor 310 may measure the weight of ball 301 to ensure it is within a predetermined range.

Further, fitness devices, such as devices 301 and 302, may measure or detect operational parameters of environmental conditions or non-instrumented or non-detected fitness devices. For example, certain activities on mat 301 may require that a user wear a specific type of footwear, such as jogging shoes. Sensors on mat 301, including but not limited to sensors 310, 312, 314, may detect or measure whether illegal footwear, such as spikes, are being worn. In certain embodiments, mat 302 may comprise one or more sensors configured to measure pressure points and/or weight distribution resulting from footwear. The system 300 may be configured to determine if the footwear comprises unauthorized pressure points, such as from wearing spikes. Unauthorized pressure points may be determined based upon predefined ranges set forth in computer-executable instructions, for example, located on memory 304.

In other embodiments, a component may be a fitness device but its sensor(s) may not be configured to measure properties that are detectable by other fitness devices. For example, in one embodiment, at least one fitness device comprises articles of footwear. For example, the footwear may comprise a sensor to measure speed (exemplary methods that may be implemented to detect speed are discussed in more detail below), however, the footwear may not comprise pressure sensors to detect unauthorized pressure points, such as the use of spikes. Therefore, while the footwear is technically a fitness device, another fitness device, such as mat 302, may be used to detect certain properties of the footwear.

In certain embodiments, a camera, such as camera 320 may also detect or measure one or more properties of a user, either before, during or after, any processes or routines disclosed herein. Camera 320 may be incorporated, either physically or logically, into one or more fitness devices, including mat 302. In other embodiments, camera 320 may be implemented into a helmet, such as a batter's helmet that may be used in baseball-related activities. In one embodiment, camera 320 may be operatively connected in a mobile terminal device, such as a cellular phone. In certain embodiments, the mobile terminal device (or any mobile device) may be a general-purpose device that comprises a memory having computer-implemented instructions that configure the device to perform as a fitness device. For example, a cellular phone may comprise software that tracks the user, such as using GPS and or location of signals, such as cellular or WI-FI signals to detect the velocity, acceleration, location or other parameters during physical activity. In this regard, those skilled in the art will readily appreciate that a camera, such as camera 320 may be associated with any type of fitness device.

In other embodiments, camera 320 may be physically or logically distinct from one or more fitness devices. In one embodiment, camera 320 may comprise any type of imaging equipment configured to capture one or more images. In one embodiment, camera 320 may be configured to capture still images, while in another embodiment; it may be configured to capture a plurality of images, such as to form a video. Camera 320 may be configured to capture any spectrum of light. For example, in certain embodiments, camera 320 may capture infra-read (IR) light. In other embodiments, camera 320 may be a plurality of cameras. Camera 320 may detect 3-dimensional motion. In further embodiments, camera 320 may be utilized in the rendering of a 3-dimensional animation of detected motion. Camera 320 may be sold as a kit with other fitness devices, including ball 301 or mat 302.

If at block 204, one or more features of a software application and/or another fitness device may be disabled or otherwise unavailable if it is determined that a criteria (parameter) is not within a predetermined range (i.e., block 206). For example, software features that assist with calculating a certain score based upon sensor data from one or more of the fitness devices 301, 302 may not be functional. In other embodiments, a score may still be permitted to be calculated, however, it will not be certified or associated with credentials if certain parameters are not within predefined ranges. In one embodiment, a fitness device comprises a ball, such as ball 301 and the predefined operational criteria may specify a range relating to: weight, dimensions, internal pressure, and combinations thereof. In one embodiment, a predetermined range may comprise a single value. For example, in one embodiment, the acceptable range for a ball is 3.3 pounds, and thus both 3.2 pounds and 3.4 pounds each would fall outside of the range.

In certain embodiments, block 208 may transmit an electronic signal configured to display a message on a display device. For example, in one embodiment, a message may be displayed for viewing by the user that indicates an error with a fitness device, such as ball 301 or mat 302. In certain embodiments, a message may indicate the detected or measured value obtained at block 206 as well as an acceptable range. Yet in other embodiments, a simpler message may merely indicate which parameter failed. In yet further embodiments, an even simpler message may indicate that a fitness device has failed a test. In addition or in lieu of displaying a message on a display device, information regarding the detected or measured parameter may be stored on a computer-readable medium, such as memory 115, or transmitted through a communication channel to a remote computer-readable medium.

If at block 204, it is determined that one or more parameters are within defined ranges, block 210 may be implemented. Block 210 may adjust one or more properties of the fitness device(s) 301, 302. The adjustment (or the determination to adjust) may be based on one or more parameters detected or measured in block 204. In other embodiments, adjustments (or related determinations) may be based upon any data obtain from sensors 101, 310, 312, and/or 314. For example, in one embodiment, sensor 314 is positioned between indicia 316 and indicia 318. If a user's height or weight is above a threshold, the distance between indicia may be increased. In one embodiment, indicias 316, 318 may be indicated by one or more Light Emitting Diodes (LEDs) and automatically adjusted. In other embodiments, mat 302 may comprise a track that allows indicia 316 or indicia 318 to be adjusted. Indeed, any mechanisms that may be configured to allow the adjustment of indicias 316, 318 are within the scope of the invention.

Block 212 may be implemented to determine or select which activity protocols to perform with fitness devices 301, 302. In one embodiment, a testing protocol configured to measure the user's performance characteristics during defined activities to provide a score may be implemented. In one embodiment, a SPARQ™ testing protocol may be selected. The selected protocol, which may be a SPARQ™ testing protocol, may be selected from a plurality of other activity protocols. An exemplary protocol may include one or more activities described within the SPARQ™ football testing protocol publically available at: http://www.nike.com/nikeos/p/sparqtraining/en_US/how_to_test?sport=football2&gender=m&user_type=athlete&test=overview (last accessed May 25, 2010), which is incorporated herein by reference in its entirety.

Figure 4:
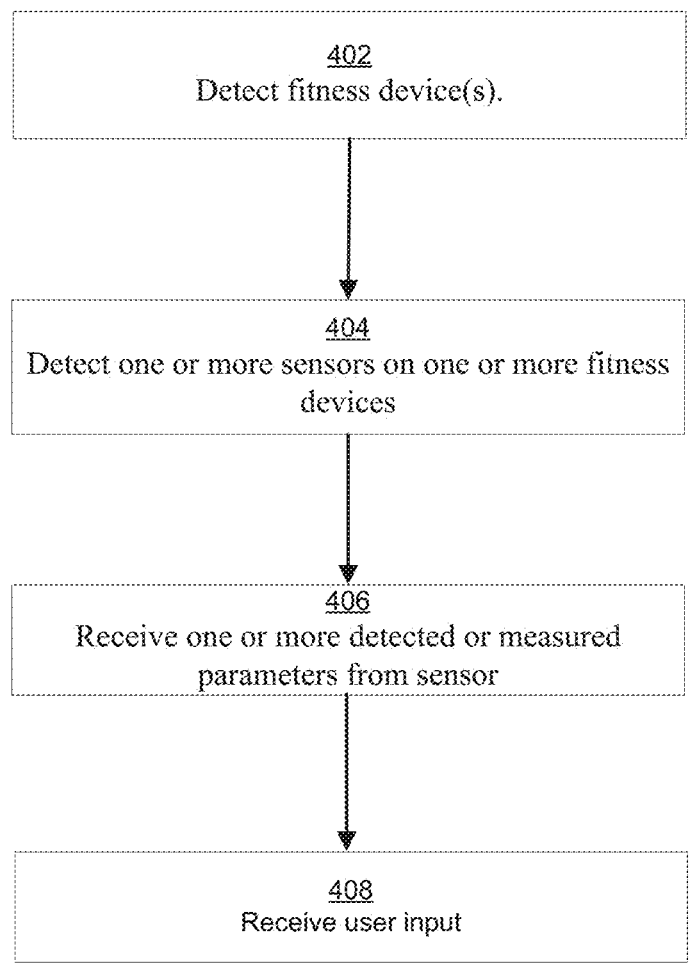
FIG. 4 is a flowchart of an exemplary method that may be implemented according to various embodiments of the invention.

One or more factors may be considered in the selection of an activity protocol. FIG. 4 shows a flowchart 400 of an exemplary method in accordance with one embodiment of the invention that may be implemented as part of selecting an activity protocol, such as in conjunction with block 212. While various blocks of FIG. 4 are shown in a linear arrangement, those skilled in the art with the benefit of this disclosure will readily appreciate that flowchart 400 is merely exemplary and that the illustrated blocks may be performed in any order, including simultaneously with one or other actions, including those activities associated with another block of flowchart 400. Further, more or fewer processes may be performed in conjunction with the selection of a protocol without departing from the scope of the invention.

Block 402 may detect one or more fitness devices. In certain embodiments, block 402 may be a part of or incorporate information or data from block 202. In other embodiments, block 402 is conducted in addition to or in lieu of block 202. In one embodiment, upon detection of ball 301 and mat 302, computer-executable instructions, such as may be located on memory 115 of electronic device 108 may be executed, such as by computing unit 113 to select a specific activity protocol. In certain embodiments, detection of certain fitness devices may allow the selection of certain protocols. For example, if mat 302 was detected, however, ball 301 was not, then at least one protocol that otherwise would be available may not be eligible for selection.

Block 404 may detect one or more sensors on one or more fitness devices, such as ball 301 or mat 302. For example, sensors 101 of ball 301 may have be interchangeable with other sensors. Therefore, in certain combinations, sensors 101 could cause the ball 301 to be off-balance or have an incorrect center of gravity. Therefore, in one embodiment, computer-executable instructions may be executed that detect the presence of one or more sensors 101 in ball 301 or other fitness device. In one embodiment, the actual placement of sensors 101 may be considered. Thus, embodiments disclosed herein envision that fitness devices may be configured so that the weights of the included sensors 101 do not change the balance or center of gravity of the fitness device 100. In certain embodiments, "certified" protocols may not be selected, or if selected may not be "certified" if a sensor or combination of sensors is detected.

In this regard, block 404 may determine if "certified" sensors are within fitness devices 301, 302. In one embodiment, less-expensive sensors may allow a user to select certain testing protocols, however, because the less-expensive sensors may not have a level of accuracy and/or precision required to certify activities conducted with the testing equipment, the measured parameters using the fitness equipment may not be certified. In certain embodiments, specific sensors may be shaped to fit in only certain arrangements in relation to certain fitness equipment, such as to ensure compliance.

Illustrative block 406 may be implemented to obtain one or more parameters from a sensor before selecting an activity protocol. The parameters may include, for example, parameters from the environment, a user, other equipment, and/or combinations thereof. In certain embodiments, parameters may be measured or detected before a selection of an activity protocol and subsequently be utilized in a selection and/or provide options for selection. For example, one or more activity protocols may be selected or made available for selection based on the user's weight and/or height or a combination of the user's weight or height. In certain embodiments, sensors 101 may measure the distance between ball 301 and mat 302. Mat 302 may be configured, such that one of sensors 406, 408, and/or 410 is configured to measure the user's weight. For example, in one embodiment, a user may be requested or required to place ball 301 on of the user's head while standing on mat 302. Those skilled in the art will appreciate that the user's weight and height are merely exemplary measurements and that other measurements or detection of parameters from one or more fitness devices would fall within the scope of the invention.

A user input may be implemented at block 408. The user input may be received, for example, through I/O interface device 117 of electronic device 117. In one embodiment, the user input may select a specific activity protocol. The selection of the protocol may be made from a plurality of available protocols. The plurality of available protocols may be based, at least in part, from one or more results obtained from other processes, including, for example, those described in relation to blocks 402-406 or other processes disclosed herein.

Figure 5:
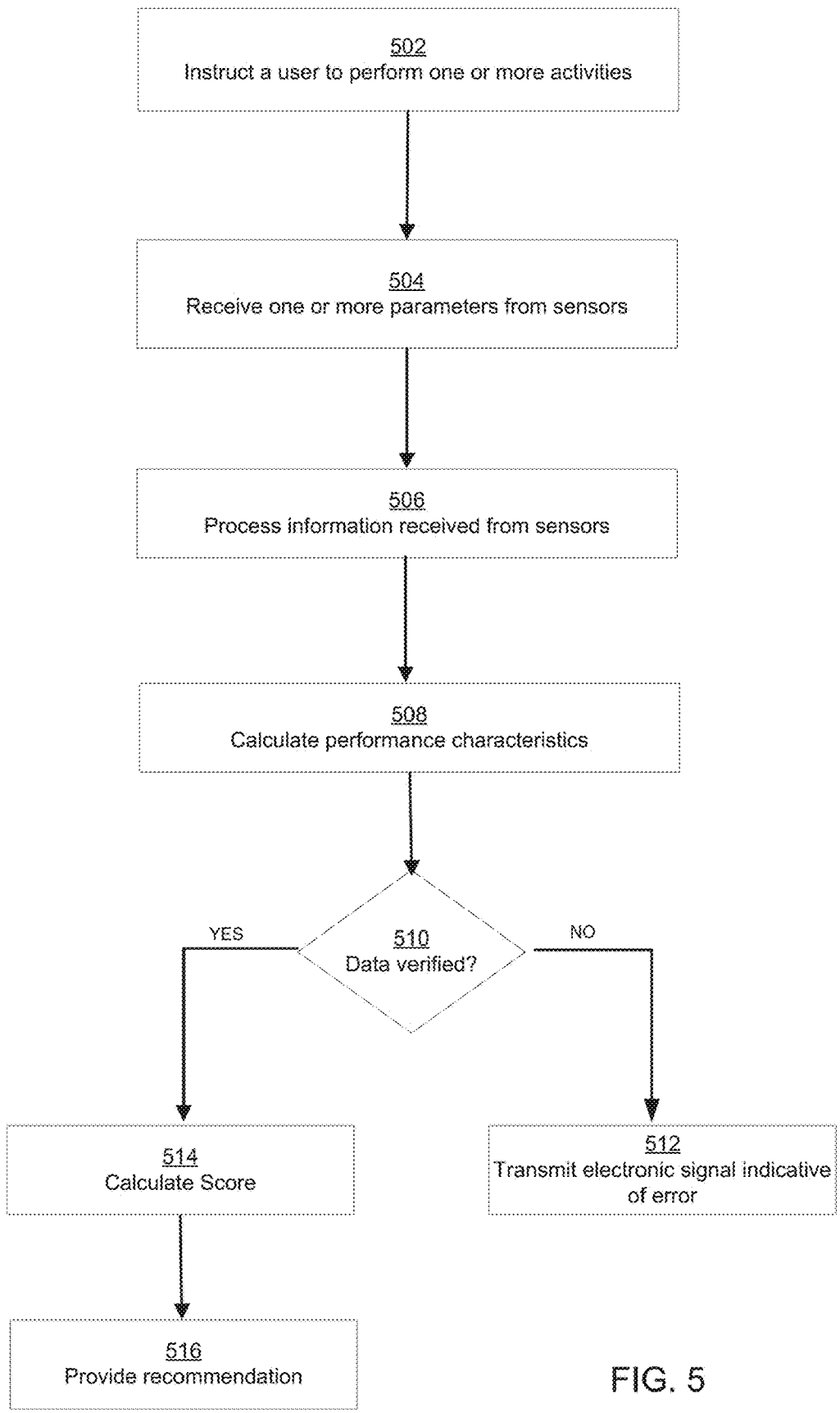
FIG. 5 is a flowchart of an exemplary method that may be implemented according to various embodiments of the invention.

Block 216 may be implemented to initiate an activity protocol. In one embodiment, the activity protocol may comprise a protocol selected at block 214. FIG. 5 is flowchart of an exemplary method of conducting an activity protocol in accordance with one embodiment of the invention. The exemplary flowchart 500 of FIG. 5 merely shows one illustrative embodiment and shall not be construed as limiting the invention to the specific embodiment. Looking to FIG. 5, a user may be instructed to perform certain activities (see, e.g., block 502). In certain embodiments, instructions may be provided by merely providing a link that the user may select, such as with a user input device operatively connected to I/O interface device 117 of electronic device 108. In further embodiments, the instructions may comprise audible components, such by indicating when a user should "start" or "stop" an activity. In still yet further embodiments, instructions may comprise a video or electronically-generated instructions, which for example, may be provided by a display device operatively connected to electronic device 108. In further embodiments, instructions may be provided in a tangible form, such as by allowing a user to print instructions on paper, such as with a printer device operatively connected to electronic device 108.

In further embodiments, instructions may be provided by transmitting an output from a fitness device, such as ball 301 or mat 302. For example, in one embodiment, indicia 316 may be a "start line" in which instructions (such as from block 502) require to start an activity that that indicia 316. Certain activity protocols may require the user to travel towards indicia 318, therefore, in certain embodiments, a visual indicator, such as an LED) may be associated with one or more of indicias 316, 318. For example, a green LED may indicate that a user starts at indicia 316 and a red LED may indicate that the user is to stop at indicia 318. In another embodiment, indicia may 318 may be associated with indicia 318 to indicate that a different starting location for an activity. In another embodiment, a portion of ball 301 may light up, vibrate or otherwise be used to signal a user. The instructions may be based upon parameters detected from one or more sensors or other devices.

Block 504 may receive one or more parameters from sensors, including sensors 101 and/or 310, 312, and 314. Further, there is no requirement that all of the received parameters are received from fitness devices. In certain embodiments, camera 320 may not be associated with a fitness device, however, parameters from camera 320 may be received at part of block 504 or any other process disclosed herein. Information from sensors, such as sensors 101, 310, 312, 314 and/or camera 320, may be processed at one or more processors, such as processor 103, processor 111, and or computing unit 113 (see, e.g., block 506). In one embodiment, raw data may be possessed. In another embodiment, data from a sensor, such as sensor 101, may be processed in accordance to a plurality of different processes. Processing of data from one sensor, such as sensor 101A may be dependent on data received from another sensor, such as sensor 101B. In other embodiments, data from a plurality of sensors, such as sensors 101 may be combined. Those skilled in the art with the benefit of this disclosure will appreciate that the exact processing of data from one or more sensors may depend on a myriad of factors, including, but not limited to, the specific activity protocol.

Data obtained from one or more sensors, such as sensors 101, 310, 312, 314 and/or camera 320 may be utilized to calculate performance characteristics (see, e.g. block 508). The data may include raw data and/or processed data. In one embodiment, the data includes data processed in accordance with block 506. One exemplary performance characteristic may include speed. Speed may be measured, such as by an accelerometer, by velocity along one or more axes. For example, speed parameters could incorporate: linear and/or lateral velocity. In other embodiments turning velocity may be considered, such as measuring the speed of a user changing directions, such as to their right or left or in the anterior or posterior direction. In certain embodiments, a multi-dimensional accelerometer may be utilized, such as to permit detecting velocity along 2 orthogonal axes. In another embodiment, an accelerometer may measure velocity along 3 orthogonal axes.

An accelerometer, either alone or in combination, with one or more additional devices, such as another sensor, may measure acceleration, inclusive of an initial or starting acceleration, deceleration, acceleration during different time-frames, and/or acceleration at specific locations. For example, sensors 310, 312, and 314 may be used to detect pressure of the user, and therefore, the location of user on mat 302. Further illustrative data may relate to, for example: distance traveled, velocity in flight, and/or power upon impact. Sensors, such as sensors 101, 310, 312, 314 may be configured to transmit and/or receive information location data, such as through wireless signals. In one embodiment, GPS data may be utilized to detect the location of a user, fitness devices 301, 302, or combinations thereof. In other embodiments, one or more sensors may comprise active or passive RFID components. For example, as a user passes within a proximity to an RFID apparatus, such as built within or attachable to mat 302, the location may be determined. In other embodiments, optical signals may assist in determining one or more performance characteristics. For example, if a user crosses a beam of light, the interruption of the light received at a sensor may indicate the location of the user, further the timing of the interruption of reception of signals (such as optical, wireless, and combinations thereof) may further provide data regarding other performance characteristics, such as velocity, and/or acceleration.

Calculation of performance characteristics may be performed using one or more algorithms or rules stored on a computer-readable medium, such as memory 115. Exemplary techniques for determining a user's speed from accelerometer signals are described in, for example, U.S. Pat. No. 6,898,550 to Blackadar et al., entitled "Monitoring Activity Of A User In Locomotion On Foot," and issued on May 24, 2005, U.S. Pat. No. 6,882,955 to Ohlenbusch et al., entitled "Monitoring Activity Of A User In Locomotion On Foot," and issued on Apr. 19, 2005, U.S. Pat. No. 6,876,947 to Darley et al., entitled "Monitoring Activity Of A User In Locomotion On Foot," and issued on Apr. 5, 2005, U.S. Pat. No. 6,493,652 to Ohlenbusch et al., entitled "Monitoring Activity Of A User In Locomotion On Foot," and issued on Dec. 10, 2002, U.S. Pat. No. 6,298,314 to Blackadar et al., entitled "Detecting The Starting And Stopping Of Movement Of A Person On Foot," and issued on Oct. 2, 2001, U.S. Pat. No. 6,052,654 to Gaudet et al., entitled "Measuring Foot Contact Time And Foot Loft Time Of A Person In Locomotion," and issued on Apr. 18, 2000, U.S. Pat. No. 6,018,705 to Gaudet et al., entitled "Measuring Foot Contact Time And Foot Loft Time Of A Person In Locomotion," and issued on Jan. 25, 2000, each of which are incorporated entirely herein by reference in their entireties for any and all purposes.

A single activity protocol may have one or more sub-components. For example, a first sub-component may be designed and/or executed to primarily measure a first athletic quality or group of qualities from a user. For example, while several performance characteristics may be collected during a portion of the activity protocol, there may be a specific theme for power, agility, speed, reaction, quickness, combinations of one or more of these characteristics, among others. Specific activities may be selected and/or grouped in an order depending on further variables, including user' characteristics, such as weight, gender, height, past performance, planned performance, goals, combinations of one or more of these characteristics among others.

Certain sports, such as football require power and speed, whereas other sports may require less power and a greater amount of speed. Therefore, different activities may be conducted to measure these characteristics. Further, different positions within team sports, such as football, often require different strengths for optimal performance. Therefore, it may be important to conduct different activity protocols for different individuals. In certain embodiments, different activity protocols may be provided to different individuals to provide different scores. For example, a soccer activity protocol may differ from a football activity protocol and results in two different scores. For example, the first score could be a "SOCCER" score, while the second score could be a "FOOTBALL" score. In yet other embodiments, all individuals may be assigned a specific score, such as an overall score to measure a collection of performance characteristics, including but not limited to: speed, agility, power, quickness, reaction and combinations thereof.

Block 510 may determine if data obtained during one or more activity protocols may be verified. In one embodiment, verification of data may compare one or more values obtained from one or more sensors, such as sensors 101, 310, 314 of fitness devices 100, 301, and 302. In certain embodiments, the received values indicate the presence or usage of certain fitness devices, such as devices 301 and 302. In such embodiments, methods substantially similar to one or more processes described above in relation to block 202 of FIG. 2 may be implemented. For example, if certain fitness devices (or specific sensors of fitness devices) are not detected, then the data may not be verified.

In further embodiments, parameters collected from sensors (i.e., sensors 101 and 310-314) may be utilized in verification process, such as presented as block 510. For example, an activity protocol may require a user to maneuver ball 301 at or around indicia 316 during a first time period and then to jump from the location of indicia 318 towards sensor 312. In such a protocol, sensor 101 of ball 301 may comprise a location-sensing apparatus and be used to ensure that an individual, other than the user, is not assisting the activity protocol. In another embodiment, the velocity of a portion of the user, such as an arm or leg, may be compared to the velocity of a fitness device, such as ball 301, to ensure the user in accurately conducting one or more activities in accordance with a specific activity protocol. Verification may consider the time in which specific activities of the activity protocol where conducted. For example, activity protocols may requires that a user conduct specific actions within a predetermined time frame. Further requirements may mandate that a second action be conducted after a predetermined time frame from a first action. In this regard, inconsistent data from one or more sensors may be detected or measured. Sensors separate from ball 301, mat 302 or other fitness devices may also be utilized to verify the data. For example, data from camera 320 may be utilized in the verification of any data from fitness devices' sensors.

Systems and methods of verification may utilize any information from any process discussed herein. For example, any information gathered, transmitted or received in relation to a process discussed within FIG. 2 and/or FIG. 5 may be utilized as part of a verification process. For example, data obtained during block 202 (detecting a fitness device) may be combined with data obtained during block 506 (processing information from sensors). In this regard, data that may have been within acceptable parameters of pre-defined criteria during the processes (i.e., blocks 202 and 506) may be may be applied, either separately or in combination, to different criteria. Further, derivations of such data may also be used, either alone or in combination, in a verification process in accordance with various embodiments.

The determination of verification may be conducted using one or more local or remote electronic devices. In one embodiment, electronic device 108 is configured to conduct one or more processes to verify data. In certain embodiments, a remote electronic device, such a server remotely located on a network may be utilized in the verification of data. In other embodiments, block 510 may be omitted and/or replaced with another process that only receives an indication of whether the data was verified.

Block 512 may be implemented if any portion of obtained data (either from a fitness device or another device, such as camera 320 when not part of a fitness device) is not verified. Block 512 may transmit (or receive) an electronic signal configured to provide an error message. In one embodiment, block 512 may incorporate one or more processes described in relation to block 208 of FIG. 2. The error message may indicate what data was not verified, why specific data could not or was not verified, suggested solutions, affected activities of the activity protocol, and combinations therefore. Further possible error messages may merely recite a code, such as an alphanumeric value. In certain embodiments, the alphanumeric value may be utilized by a third-party to identify one or more problems with the data, fitness device, activity protocol, and combinations thereof. In certain embodiments, a code may not be readily decipherable by the user. This may be advantageous to prevent users from attempting unauthorized activities to depress or circumvent an error in an attempt to inaccurately conduct an activity protocol. An error message may be transmitted to one or more electronic devices, including electronic device 108. In certain embodiments, the message may be transmitted to another device, such as a mobile terminal device. There is no requirement that the error message utilize alphanumeric values. In certain embodiments, the error message may use audio, visual, or audiovisual cues to indicate at least a portion of data collected could not or was not verified.

If, however, at least a portion of data was verified at block 510, a score may be calculated (see, e.g., block 514). As discussed above, the score may be based upon the activity protocol, user characteristics, and/or other variables. The calculation may be based on one or more performance characteristics of block 508. In this regard, calculating a score may be based, at least in part, on the inclusion of specific data and/or weighting of specific performance characteristics. Calculation of the score may be conducted at one or more local or remote processors, including but not limited to: processor 103, processor 111, and or computing unit 113. In certain embodiment, a score may be formulated based upon one or more sub-scores. For example, sub-scores may be calculated for specific characteristics, such as for example, speed, responsiveness, quickness, and/or power. In certain embodiments, the user may be provided only a single score, however, the sub-scores may be utilized, such as in block 516, to provide recommendations for improving a user's score.

Block 516 may be implemented to provide recommendations to improve a user's score. As discussed above, the recommendations may be based, at least in part, upon one or more sub-scores, or upon a portion of collected data. For example, a specific sub-score is not required to be calculated, but rather data, either raw or processed, may be used to provide recommendations. Recommendations may include an indication of specific performance characteristics, specific activities with an activity protocol, or combinations thereof. Recommendations may include a recitation of activities that were not conducted during one or more activity protocols.

Historical data may be utilized as part of block 516. Exemplary historical data may include sensor data collected from previous activity protocols. For example, it may indicate that a user has increased or decreased his or her performance during certain activities. Further historical data may include information regarding other individuals, such as other individuals who have conducted the same or similar activity protocols. The data may be limited to others having similar user characteristics, including for example, gender and/or age. Block 516 may consider the user's goals or preferred level of performance. For example, if the user is a high-school football player who wants to play Division I college football, block 516 may utilize this data to provide recommendations. Providing data obtained from other individuals may fuel competition and/or motivation to maintain an exercise routine. Further, the recommended routine may be more helpful to assist the individual to reach a specific goal. In certain embodiments, data may be associated with identifying information of third-parties. For example, the user's data may be compared against data from a plurality of individuals. In one embodiment, local individuals having predefined characteristics, such as similar scores, subscores, performance characteristics, demographic qualities, and combinations thereof may be identified. The user may be provided an opportunity to contact, either directly or indirectly, with other individuals. This may be beneficial, for example, to motivate the user by providing competition and/or may use fitness devices 100, 301, 302 together.

As additional example aspects of this invention, one or more elements or components of a fitness device or electronic device may be marketed, sold, or utilized as a kit. One such embodiment may include a kit comprising Kits may be associated with instructions for constructing a fitness device, including using one or more specific sensors with one or more fitness devices. Further instructions may indicate how to use one or more fitness devices during one or more activity protocols. In certain embodiments, instructions may be provided that indicate exemplary methods for using one or more fitness devices with one or more additional electronic devices to generate a score. Those skilled in the art will readily appreciate any instructions are not required to be printed and remain physically present with the other components of the kit, but rather the instructions may be provided on a computer-readable medium. Such instructions may reside on a server that the user may access. In accordance with certain embodiments, the user may be provided information, such as a link to an address on the Internet, which comprises the instructions, which would fall within the scope of providing instructions. Thus, as used herein, providing instructions is not limited to printed copies that are deliverable with a fitness device.

While the invention has been described in detail in terms of specific examples including presently preferred modes of carrying out the invention, those skilled in the art will appreciate that there are numerous variations and permutations of the above described systems and methods. Thus, the spirit and scope of the invention should be construed broadly as set forth in the appended claims.

I claim:

1. A method of evaluating performance characteristics of a user, comprising:
   electronically detecting at a first electronic device, a ball comprising at least two sensors, wherein a first sensor of the at least two sensors of the ball is configured to measure a first parameter and a second sensor of the at least two sensors of the ball is configured to measure an operational criterion of the ball;
   receiving at the first electronic device, a signal from the second sensor indicative of an internal pressure of the ball associated with a grip applied to the ball; and
   selecting, by the first electronic device when the internal pressure of the ball meets a predefined threshold of the operational criterion, at least a first activity protocol of a plurality of activity protocols to be available for subsequent selection by the user of the first electronic device.

2. The method of claim 1, wherein the first parameter comprises one of velocity, acceleration, location, energy transfer, temperature, orientation, light, sound, magnetism, or a particular motion along two or more axes.

3. The method of claim 2, further comprising:
   calculating a plurality of performance characteristics from data collected from the at least two sensors of the ball during the user's performance of the first activity protocol.

4. The method of claim 3, wherein the performance characteristics are selected from the group consisting of: power, agility, speed, reaction, quickness, and combinations thereof.

5. The method of claim 3, further comprising:
   receiving data from a third sensor of a second electronic device; and
   cross-referencing data collected from the at least two sensors of the ball and the third sensor of the second electronic device to validate actions selected from the group consisting of: timing between two user actions, timing of a specific user action, location of the user, location of a fitness device, velocity of the user, velocity of the fitness device, acceleration of the user, acceleration of the fitness device, detection of a fourth sensor, detection of the fitness device, and combinations thereof.

6. The method of claim 1, wherein the predefined threshold of the operational criterion specifies a range relating to the internal pressure of the ball.

7. The method of claim 1, further comprising:
   using the at least two sensors of the ball to determine if an apparatus external to the ball meets a predefined threshold of an operational criterion of the apparatus.

* * * * *